United States Patent [19]

Ozaki et al.

[11] Patent Number: 5,564,418

[45] Date of Patent: Oct. 15, 1996

[54] DIAGNOSTIC DEVICE FOR MEASURING INFORMATION ON BLOOD IN A LIVING OBJECT

[75] Inventors: Takeo Ozaki; Susumu Suzuki, both of Hamamatsu, Japan

[73] Assignee: Hamamatsu Photonics K.K., Shizuoka-ken, Japan

[21] Appl. No.: 219,294

[22] Filed: Mar. 28, 1994

[30] Foreign Application Priority Data

Mar. 26, 1993 [JP] Japan .................................. 5-092158

[51] Int. Cl.$^6$ ...................................................... A61B 5/00
[52] U.S. Cl. ........................... 128/633; 128/666; 128/691
[58] Field of Search ........................... 128/633–4, 664–7, 128/691–2, 694

[56] References Cited

U.S. PATENT DOCUMENTS

| | | | |
|---|---|---|---|
| 4,281,645 | 8/1981 | Jobsis | 128/633 |
| 5,101,825 | 4/1992 | Gravenstein et al. | 128/633 |
| 5,103,829 | 4/1992 | Suzuki et al. | 128/633 |
| 5,195,963 | 3/1993 | Yafuso et al. | 128/692 X |
| 5,282,467 | 2/1994 | Piantadosi et al. | 128/633 |
| 5,383,468 | 1/1995 | Nakayama et al. | 128/713 |

FOREIGN PATENT DOCUMENTS

| | | |
|---|---|---|
| 0502270 | 9/1991 | European Pat. Off. . |
| 0615723 | 9/1994 | European Pat. Off. . |

OTHER PUBLICATIONS

J. P. P. M. De Vries et al "Continuous Measurement of Blood Volume during Hemodialysis by an Optical Method" *ASAIO Transactions*, vol. 38, No. 3 pp. 181–185, Jul. 1992.

M. Vegfors et al "Accuracy of pulse oximetry at various haematocrits and during haemolysis in an invitro model" *Medical & Biological Engineering & Computing*, vol. 31, No. 2 pp. 135–141, Mar. 1993.

*Cotside Measurement of Cerebral Blood Flow in Ill Newborn Infants by Near Infrared Spectroscopy*, A. D. Edwards et al., The Lancet, Oct. 1, 1988, pp. 770–771.

*Quantification of Cerebral Oxygenation and Haemodynamics in Sick Newborn Infants by Near Infrared Spectrophotometry*, J. S. Wyatt et al., The Lancet, Nov. 8, 1986, pp. 1063–1066.

*Primary Examiner*—Angela D. Sykes
*Attorney, Agent, or Firm*—Sughrue, Mion, Zinn, Macpeak & Seas

[57] ABSTRACT

Perform measurement of blood flow using physiological salt solution, which is harmless to living objects, as a tracer. The head portion (4) of a subject is alternately irradiated with laser light 1, and laser light 2. The light exiting from the head portion (4) is detected and converted to an electric signal. By performing a first calculation on this electric signal, a CPU (1) outputs a signal representing the change in concentration of hemoglobin in the head (4). Further, a second calculation process is performed on the electric signal which represents changes in concentration of hemoglobin generated by injection of the physiological salt solution. At least one of the blood flow or the absolute concentration of oxyhemoglobin and deoxyhemoglobin is displayed. Because a material safe to living objects is used as the tracer, measurement of the blood flow can be safely and repeatedly performed.

14 Claims, 5 Drawing Sheets

CHANGE IN CONCENTRATION OF HbO₂ (△HbO₂)

CHANGE IN CONCENTRATION OF Hb (△Hb)

CHANGE IN CONCENTRATION OF (HbO₂ + Hb)

DIAGNOSTIC DEVICE FOR MEASURING INFORMATION ON BLOOD IN A LIVING OBJECT

BACKGROUND OF THE INVENTION

1. Field of the Invention

The present invention relates to a diagnostic device that measures at least blood flow, oxygen saturation level in the blood, or the absolute concentration of hemoglobin of blood in a living object injected with a liquid (for example, a physiological salt solution) that is safe for living objects.

2. Description of the Related Art

Supply of blood to various organs of living objects is an essential factor for maintaining the life of living objects and for living objects to function properly. Blood supply to the brain is particularly important. Measuring cerebral blood flow is an indispensable tool for patients where there is a danger of the brain falling into a critical condition. In one conventional technique, a radioactive substance, such as radioactive xenon, is injected into a living object as a tracer. Changes in the tracer are measured by a γ-ray sensor attached to the head of a subject under investigation. Blood flow is then calculated. In another technique, the tracer injected is a pigment, such as cardio-green. By monitoring the flow of the pigment according to changes in the amount of light irradiated from an external source that is absorbed by the pigment. The blood flow is then calculated.

U.S. Pat. No. 4,281,645 describes a device for measuring changes in blood oxygen and blood concentration in the brain (not cerebral blood flow itself). This device uses near-infrared (NIR) light as a light source. Living tissue is comparatively transparent to NIR light. The device also uses an extremely sensitive sensor, such as a photomultiplier tube, in the optical detector. Although previously only measurements of thin body portions such as finger tips and ear lobes was possible, this device allows measurements of the head. This reference describes clinical monitoring of the head which allows measurements of changes in concentration of oxyhemoglobin ($HbO_2$) and deoxyhemoglobin (Hb) in the blood in the head.

There have been known the following problems with the above-described device. Measurements can not be repeatedly performed, because tracers such as pigments and radioactive materials are undesirable to living objects. Also, countries and organizations often prohibit injecting these tracers into human subjects. Although more stable and more precise than another conventional technique using the Doppler effect which measures blood flow from the wavelength shift of an ultrasonic wave, measurement of blood flow using such tracers is difficult in a clinical situation. Although a device (hereinafter referred to as an NIR monitor) which measures changes in blood concentration and blood oxygen in the head using NIR light can measure the relative change in oxyhemoglobin ($HbO_2$) and deoxyhemoglobin (Hb), it can not obtain the absolute value, and so direct information relating to the important cerebral blood flow can not be obtained.

SUMMARY OF THE INVENTION

It is an objective of the present invention to provide a diagnostic device that solves the above-described problems by using a material harmless to living objects as a tracer and measuring information relating to flood flow.

In order to achieve the above-described objectives, a diagnostic device according to the present invention comprises irradiation means for irradiating light on a predetermined position of a part of a living object, such as a head, detection means for detecting light derived from the living object, converting means for converting the detected light into a first electric signal, and calculation means. The calculation means performs a first calculation process on the first electric signal to output a second electric signal representing a change in concentration of hemoglobin at the predetermined position of the part of the living object. The change in concentration of hemoglobin is caused by injecting a blood diluting liquid, such as physiological salt solution, into the living object. The calculation means subsequently performs a second calculation process on the second electric signal to calculate at least one of a blood flow, a degree of oxidation of hemoglobin, and an absolute concentration of hemoglobin.

When the calculation means calculates the blood flow in the predetermined position of the part of the living object, the calculation is performed on the basis of the absolute concentration of hemoglobin calculated by the calculation means. The calculation means calculates a passage time required for the blood diluting liquid injected into the living object to pass the predetermined position of the part of the living object, and the blood flow is obtained based on the calculated passage time.

Preferably, the calculating means outputs a third signal representing changes in concentration of oxyhemoglobin and a fourth signal representing changes in concentration of deoxyhemoglobin. The calculating means calculates at least one of the blood flow, the degree of oxidation of hemoglobin and the absolute concentration of hemoglobin based on at least one of the third signal and the fourth signal.

The irradiation means alternately irradiates the predetermined position of the part of the living object with light having at least two types of wavelength to obtain the third signal and the fourth signal. The light irradiated by the irradiation means to obtain the third signal and the fourth signal has wavelengths of about 775 nm and about 825 nm, respectively. The physiological salt solution used as the blood diluting liquid has a light absorption coefficient which is negligibly smaller than light absorption coefficients of oxyhemoglobin and deoxyhemoglobin.

According to another aspect of the invention, there is provided a diagnostic device which comprises blood volume measuring means, such as NIR monitoring device, for measuring a volume of blood existing in a part of a living object and providing a measured value of the blood of volume. Injection means is provided for injecting physiological salt solution into the living object. Time measuring means is further provided for measuring a time required for the physiological salt solution to pass through a predetermined position of the part of the living object. Computing means is yet further provided for computing a blood flow based on the measured value of the blood of volume and the passage time.

Preferably, the blood volume measuring means comprises a light source irradiating near-infrared light on the predetermined position of the part of the living object, a photomultiplier tube receiving the near-infrared light derived from the living object, and processing unit processing the near-infrared light derived from the living object to calculate the volume of blood.

The time measuring means comprises integrating means for integrating a change in concentration of hemoglobin and producing an integrated value, detecting means for a maximum change in concentration of hemoglobin and producing a maximum value, the time measuring means calculating the passage time based on the integrated value and the maximum value. The integrating means comprises first detection means for detecting a start time at which the physiological salt solution starts passing the predetermined position of the part of the living object, and second detection means for detecting an end time at which the physiological salt solution ends passing the predetermined position. The integrating means performs integration of the change in concentration of hemoglobin in a range between the start time and the end time. The computing means outputs a first signal representing changes in concentration of oxyhemoglobin and a second signal representing changes in concentration of deoxyhemoglobin, and wherein the calculating means calculates at least one of the blood flow, a degree of oxidation of hemoglobin and an absolute concentration of hemoglobin based on at least one of the first signal and the second signal.

BRIEF DESCRIPTION OF THE DRAWINGS

The above and other objects, features and advantages of the invention will become more apparent from reading the following description of the preferred embodiment taken in connection with the accompanying drawings in which.

DETAILED DESCRIPTION OF THE PREFERRED EMBODIMENTS

Figure 1:
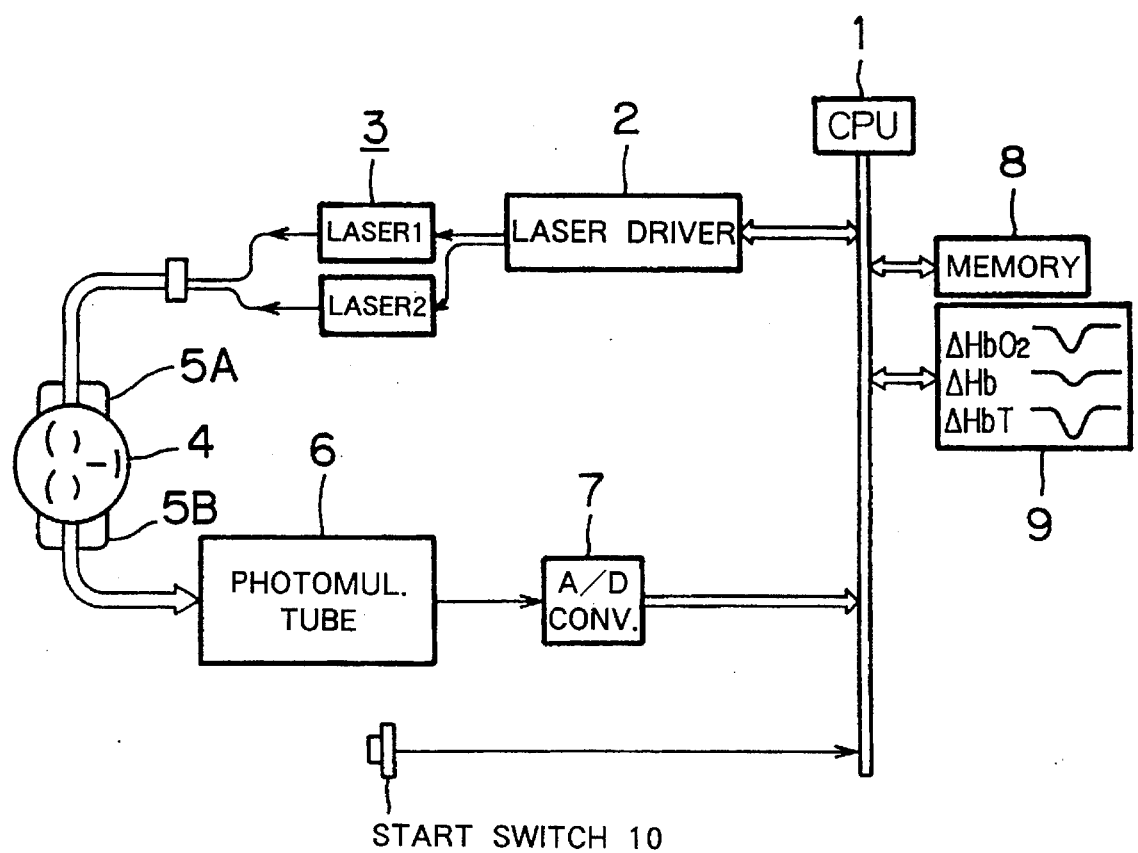
FIG. 1 is a schematic block diagram showing a diagnostic device according to an embodiment of the present invention.

A diagnostic device according to a preferred embodiment of the present invention will be described while referring to the accompanying drawings wherein like parts and components are designated by the same reference numerals to avoid duplicating description.

FIG. 1 shows a schematic structural diagram of the diagnostic device according to an embodiment of the present invention. In FIG. 1, a light source 3 is connected to a central processing unit (hereinafter referred to as a CPU) 1 via a laser driver 2. Two types of different wavelength light are outputted by the light source 3: laser light 1 with wavelength $\lambda_1$ and laser light 2 with wavelength $\lambda_2$. Laser light wavelength $\lambda_1$ is 775 nm and laser light wavelength $\lambda_2$ is 825 nm. These laser light wavelengths are alternately outputted based on the control of the CPU 1. The laser light 1 with wavelength $\lambda_1$ and laser light 2 with wavelength $\lambda_2$ are for measuring the concentration of oxyhemoglobin ($HbO_2$) and deoxyhemoglobin (Hb).

An irradiation-side fastener 5A is attached to the head 4 of the test subject for irradiating the head 4 of the test subject with laser light outputted by the light source 3. The irradiation-side fastener 5A supports the tip of a bundle of optical fibers for guiding the laser light. A detection-side fastener 5B is fastened at a predetermined interval (5 to 6 cm) from the irradiation-side fastener 5A. The distance between the irradiate-side fastener 5A and the detection-side fastener 5B is the length of the optical pathway. The laser light detected by the detection-side fastener 5B is guided toward a photomultiplier tube 6 by optical fibers. After the output from the photomultiplier tube 6 is subjected to analog-to-digital conversion at an analog/digital converter 7, it is stored in a memory 8 at a predetermined timing. A signal is stored in the memory 8 every 0.5 seconds. The CPU 1 outputs changes in concentration of oxyhemoglobin $\Delta HbO_2$, the change in concentration of deoxyhemoglobin $\Delta Hb$, and the change concentration of total hemoglobin $\Delta HbT$ ($HbT=HbO_2+Hb$) to an output device 9 every 0.5 seconds. Parameters necessary for the CPU 1 to perform various calculations and programs for driving the CPU 1 are stored in the memory 8. The start switch 10 is for advising the CPU 1 that a measurement of blood flow has started.

The present embodiment measures the absolute value of the level of oxygen saturation cerebral blood flow ($SO_2$) and the cerebral blood flow (F) using physiological salt solution as a tracer simultaneously with the absolute concentration of the oxyhemoglobin ($HbO_2$) and deoxyhemoglobin (Hb). The physiological salt solution used as a tracer is itself a body fluid and so is harmless to the human body. Liquids other than physiological salt solution can be used for diluting the blood if they have an absorption coefficient negligible compared to that of hemoglobin in the wavelength range of the utilized laser light and moreover if the safety to living objects is assured.

(1) Measurement of blood flow

The cerebral blood flow F is the amount of blood flowing to the brain during a unit of time. Blood flow can be determined using the following formula:

$$F=V/T,$$

where

V is the volume of blood in the brain; and

T is the time required for V amount of blood to pass through the brain. The volume of blood in the brain can be measured using, for example, a near infrared (NIR) monitor. Therefore, the cerebral flow F can be determined by determining passage time T. When measuring with an NIR monitor, the volume of blood in the brain will be displayed in units of either ml/100 g of brain or concentration of hemoglobin in μmoles/liter. If the passage time T is displayed in seconds, the cerebral blood flow will be displayed in ml/100 g of brain/second or μmoles/liter/second.

Below the measurement method of the passage time T will be described.

Figure 2:
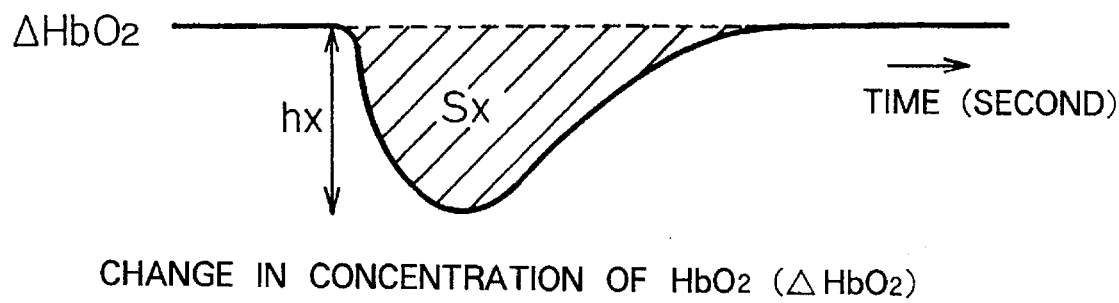
FIG. 2(a) is a graphical representation showing change in concentration of oxyhemoglobin.
FIG. 2(b) is a graphical representation showing change in concentration of deoxyhemoglobin.
FIG. 2(c) is a graphical representation showing change in concentration in the total volume of hemoglobin.
Figure 2:
Figure 2:
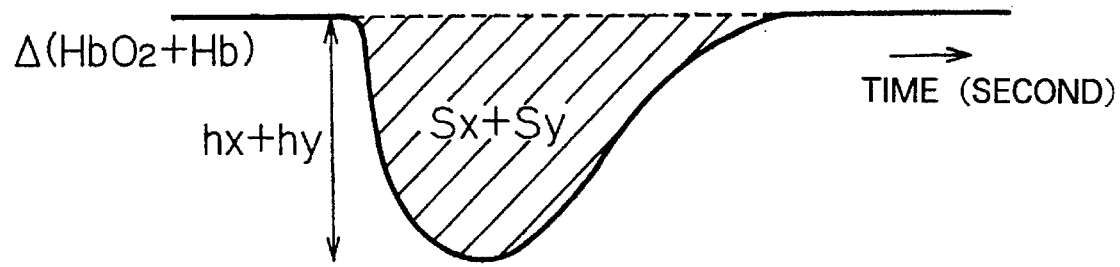

Injecting physiological salt solution into an artery slightly dilutes the portion of the blood into which the solution was injected. This condition is virtually maintained until the blood reaches the brain. Afterward, the blood passes through capillary vessels and leaves the head after entering the veins therein. An NIR monitor is mounted to the head and the change in hemoglobin ($HbO_2$ and Hb) in the brain is monitored. When several centiliters of physiological salt solution is injected over a short period of time, μmoles/liter order changes in concentration of hemoglobin (the hemoglobin dilution) in the head are observed over a period of several seconds to several tens of seconds. FIG. 2 is a graph showing the change in concentration of hemoglobin. FIG. 2(a) shows the change in concentration of oxyhemoglobin, $\Delta HbO_2$, FIG. 2(b) shows the change in concentration of deoxyhemoglobin, $\Delta Hb$, and FIG. 2(c) shows the change in concentration in the total volume of hemoglobin, $\Delta(HbO_2+Hb)$.

The passage time T required for physiological salt solution injected into an artery to pass a measurement position in a part of the brain has applied to it a value determined by dividing the integral value S of the change in concentration of the blood by the maximum volume h of change in concentration (T=S/h). When physiological salt solution is injected into the blood, the blood is diluted and the concentration of the hemoglobin ($HbO_2+Hb$) drops. The change in concentration of the hemoglobin is measured at a predetermined interval to determine the total measured value (S) and the maximum amount of the change in concentration (h), thus obtaining the passage time T.

The oxyhemoglobin ($HbO_2$) and deoxyhemoglobin (Hb) are diluted with the injected physiological salt solution at the same rate and so the form of their concentration changes is the same. Therefore, no matter which of the curves in FIGS. 2(a) through 2(c) are used, the value obtained by dividing the area of the change portion by the maximum change amount provides the same result (i.e., T=Sx/hx=Sy/hy=(Sx+Sy)/(hx+hy)).

The passage time T can also be determined based on the graph created by taking the relative value of the measured concentration of the hemoglobin along the vertical axis. That is, the passage time T can be determined by applying only the shape of the change in concentration of the oxyhemoglobin ($HbO_2$) or the deoxyhemoglobin (Hb).

Figure 4:
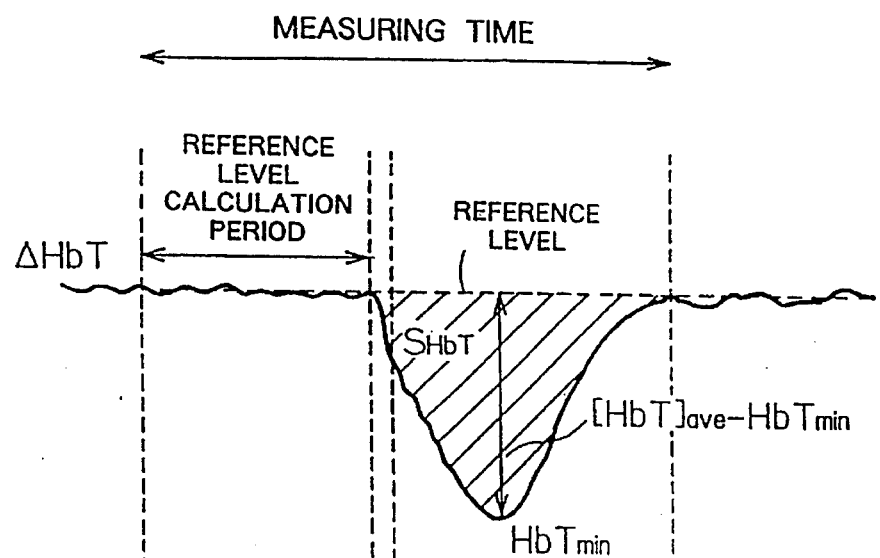
FIGS. 4(a) and 4(b) are graphical representations showing changes in concentration in volume of total hemoglobin and changes in concentration in oxyhemoglobin, respectively, for describing a method of determining passage time of physiological salt solution injected into the blood stream.
Figure 4:
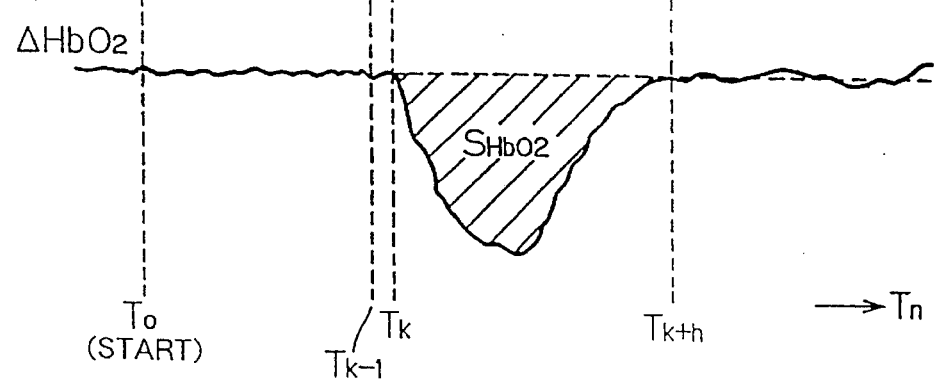

A concrete method for determining the passage time T will be described while referring to FIGS. 4 and 5. In the present embodiment, the changes in volume of both oxyhemoglobin ($HbO_2$) and deoxyhemoglobin (Hb) are determined. Passage time T is determined based on the change in volume of the total hemoglobin ($HbT=HbO_2+Hb$). This is because the change in volume of total hemoglobin is greater than either the change in volume of oxyhemoglobin ($HbO_2$) or deoxyhemoglobin (Hb).

An operator presses the switch 10 and injects a predetermined amount of physiological salt solution into the living object. The CPU 1 receives the signal outputted from the start switch 10 and performs initialization of the parameters k and h in step S1. Afterward, the time point Tk when the $\Delta HbT$ starts to decrease because of the injected physiological salt solution is detected. The detection of the time point Tk is accomplished by finding a time point when the concentration drops "a" μ moles or more from the value of $\Delta HbT(To)$ representing the level of $\Delta HbT$ when the start switch 10 is pushed, as shown in FIG. 4(a) (steps S2 and S3). The value of "a" is selected depending on the amount of noise contained in the signal to be measured. Generally, it is desirable that 1/10 of the maximum reduction level of the $\Delta HbT$ curve be determined as the value of "a". When Tk is detected, the average amount of the $\Delta HbT$ from To to Tk-1 is calculated to determine a reference level [HbT]ave. After Tk, while the physiological salt solution is passing, the $\Delta HbT$ will show a value smaller than [HbT]ave. The point in time Tk+h when this again increases larger than the [HbT]ave is detected in step S5. Further, the minimum value HbTmin of the $\Delta HbT$ is detected in step S7. At this point, data collection is stopped and later calculation of necessary values are performed.

First, the total of the change in concentration of $HbO_2$ and HbT during the time from Tk to Tk+h are determined in step S8. That is, the areas SHbT and $SHbO_2$ of the hashed areas shown in FIGS. 4(a) and 4(b) are determined, the degree of oxygen saturation $SO_2$ is calculated, and the result is displayed on the output device 8 in step S9. The oxygen saturation level $SO_2$ is applied to the ratio between the total amount of change in concentration of $HbO_2$ and HbT. Next, the passage time T is calculated. The result is displayed by the output device 9 in step S10. The passage time T is calculated based on the maximum value of the change in concentration of HbT and the total SHbT of the change in concentration of HbT. Because the maximum value of the change in concentration of HbT is the difference between the reference level [HbT]ave of HbT determined in step S4 and the minimum value HbTmin of HbT detected in step S7, the passage time T can be determined with the following formula:

$$T=SHbT/\{[HbT]ave-HbTmin\}.$$

This finishes the algorithm for determining the passage time.

The cerebral blood flow (F) is determined with calculations using the formula F=V/T based on the passage time T obtained from the above calculations and the volume V (cc/cm$^3$ or μmoles) of cerebral blood as measured separately. This calculation is also performed using the CPU 1. The results are displayed on the output device 9. The method of measuring the cerebral blood volume (V) is described in the 1990 edition of "The Journal for the American Physiological Science Conference", pp 1086 to 1091.

Figure 5:
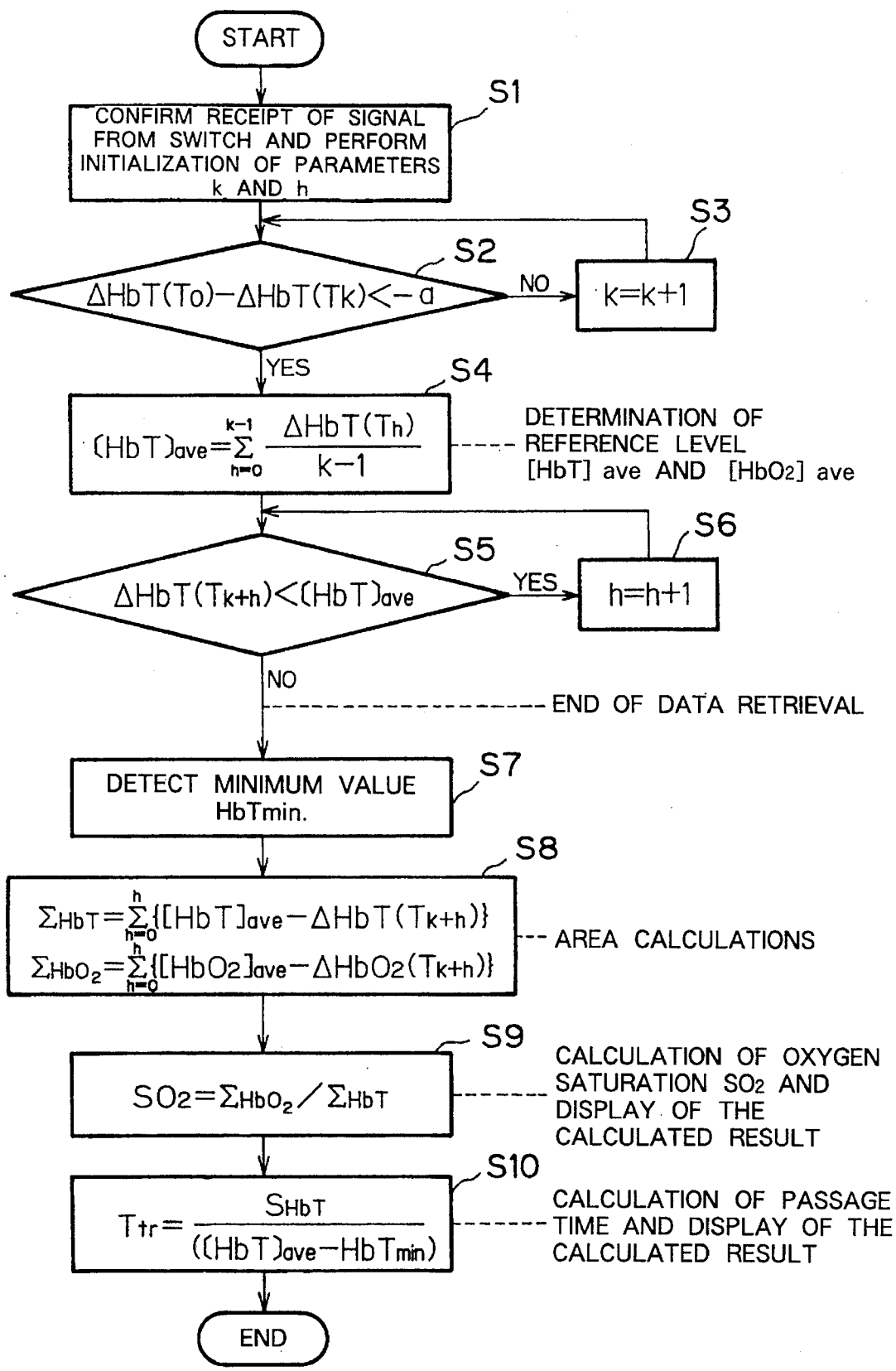
FIG. 5 is a flow chart showing procedure for determining passage time.

(2) Measurement of absolute value of oxygen saturation ($SO_2$) in cerebral blood flow The absolute value of oxygen saturation ($SO_2$) in cerebral blood flow is determined by calculating the ratio between SHbT in regards to $SHbO_2$ as determined in step S9 in FIG. 5. This is equivalent to the ratio of the amount of change corresponding to the oxyhemoglobin and the total hemoglobin. For example, by the maximum value of the change in concentration of deoxyhemoglobin and oxyhemoglobin hx and by, the level of oxygen saturation in cerebral blood is determined by the formula:

$$So_2=hx/(hx+hy).$$

As described above, along with the injection of physiological salt solution, oxyhemoglobin ($HbO_2$) and deoxyhemoglobin (Hb) are diluted in the same way. Therefore the changes in their volumes is proportional to the concentration itself. In FIGS. 2(a) through 2(c), if the ratio of hx to hy is three to one, then the ratio of the concentration of $HBO_2$ to Hb is also three to one and the absolute value of the level of oxygen saturation in hemoglobin is 75%. Components necessary for this calculation are the change in total amount (Sx, Sy) of change in concentration of oxyhemoglobin ($HbO_2$) and deoxyhemoglobin (Hb) or the maximum value (hx and hy) of the change in concentration. Therefore, all that needs to be known is the shape of the change. The vertical axis in FIGS. 2(a) through 2(c) can be the relative value of the change in concentration. This means that after quantitating the change in concentration, measurement can be made without relation to the weak point of NIR monitors, i.e., the need for assuming the average distance travelled by the light (the optical pathway).

(3) Measurement of the absolute concentration of $HbO_2$ and Hb

By measuring the change in concentration of oxyhemoglobin ($HbO_2$) and deoxyhemoglobin (Hb) at least two points in time wherein the concentration of hemoglobin differs, the absolute concentration of these can be determined.

Figure 3:
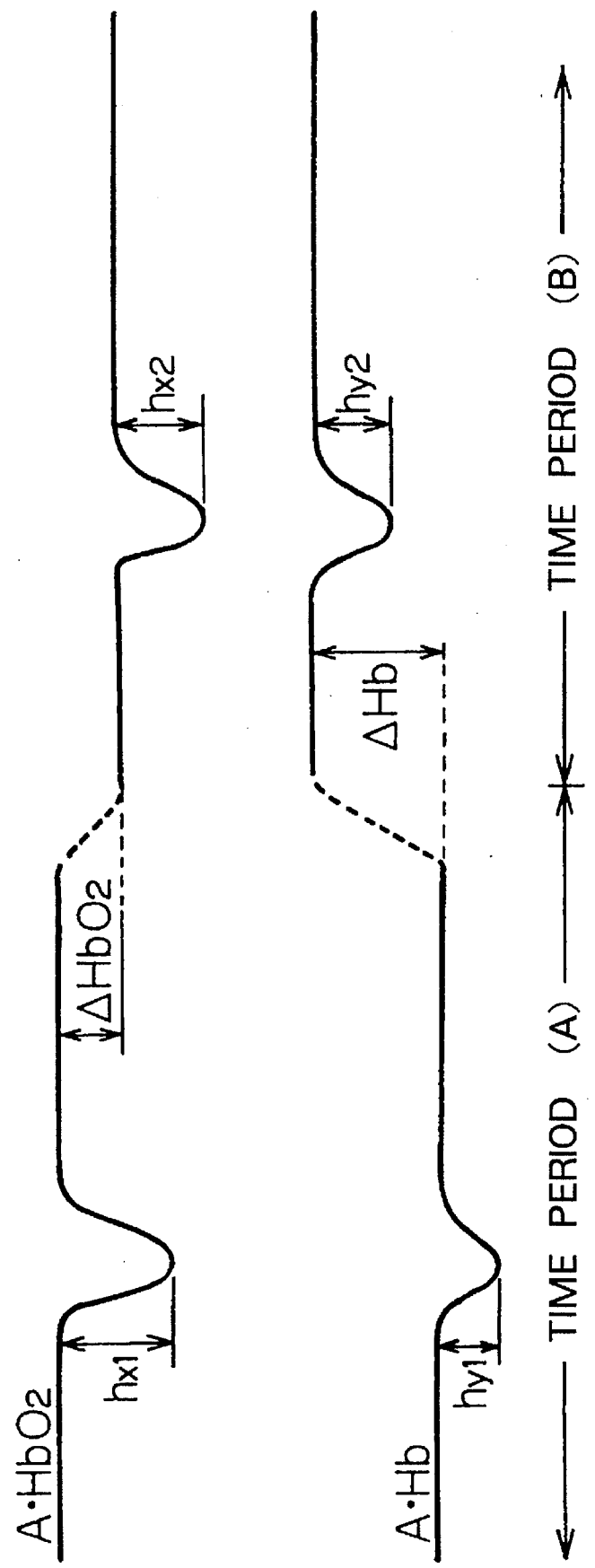
FIG. 3 a graphical representation showing changes in concentration of hemoglobin measured over several times.

As shown in FIG. 3, the change in concentration of oxyhemoglobin hx1 and the change in concentration of deoxyhemoglobin hy1 are measured in the first measurement of blood flow performed at time period (A). The change in concentration of oxyhemoglobin hx2 and the change in concentration of deoxyhemoglobin hy2 are measured in the same way also at the second measurement of blood flow performed during time period (B). Further, the differences between the average concentrations measured in the first and second blood flow measurements for both oxyhemoglobin and deoxyhemoglobin are determined. Assuming that the absolute concentration of oxyhemoglobin and deoxyhemoglobin during time period (A) are $AHbO_2$ and $AHb$ respectively, the following equation can be formed:

$AHbO_2:AHb=hx1:hy1$ $(AHbO_2+\Delta HbO_2):(AHb+\Delta Hb)=hx2:hy2$

From the above equations, the following can be determined:

$AHbO_2=\{hx1/(hy2\times hx1-hy1\times hx2)\}\times(\Delta Hb\times hx2-\Delta HbO_2\times hy2)$ $AHb=\{hy1/(hy2\times hx1-hy1\times hx2)\}\times(\Delta Hb\times hx2-\Delta HbO_2\times hy2)$ By setting the sum of $AHbO_2$ and $AHb$ determined by the above method as the new cerebral blood volume V, this can be used in new blood flow calculations. At this time, when the second blood flow measurement is performed, after the first measurement (processing and calculation in FIG. 5) is finished, the CPU 1 monitors how much the present data $\Delta HbO_2(t)$, $\Delta Hb(t)$ has changed from the values for $[HbO_2]$ ave/1, [Hb]ave/1 measured in the first measurement. When it exceeds a predetermined amount M, display is performed and that a second measurement is possible is advised. The predetermined amount M is normally set to about 5 μmoles, although this will vary with the amount of noise included in the measured value. After viewing this display, the operator will perform the second measurement (process and calculation in FIG. 5). The results of the second measurement are calculated by the CPU 1. The calculation portion determines the cerebral blood volume V, that is, the absolute concentration $\Delta HbT$ (μmoles) of total hemoglobin from the results of the first and second measurements. Cerebral blood flow is newly calculated based on the thus-determined cerebral blood volume V.

The above-described embodiment described determining cerebral blood flow. However, the present invention is not limited to this. Blood flow in organs other than the brain can be determined using the same method.

As described above, according to the present invention, a body fluid (for example, physiological salt solution) with absolutely no harmful effects on living tissue is used to dilute the blood as a tracer. Therefore, measurement of blood flow can be performed safely and repeatedly. Measurement of the absolute value of oxygen saturation in blood and measurement of the absolute concentration of hemoglobin, both of which have been impossible using conventional NIR monitor devices, is possible. Because measurement of blood flow is possible based on the blood volume displayed by the hemoglobin concentration, this becomes a great resource to clinical diagnosis, especially of the brain.

While the invention has been described in detail with reference to specific embodiments thereof, it would be apparent to those skilled in the art that various changes and modifications may be made therein without departing from the spirit of the invention. For example, the laser light wavelength $\lambda_1$ may not precisely be 775 nm but be a wavelength in the vicinity thereof. Likewise, the laser light wavelength $\lambda_2$ may not precisely be 825 nm but be a wavelength in the vicinity of 825 nm.

What is claimed is:

1. A diagnostic device comprising:
   irradiation means for irradiating light on a predetermined position of a part of a living object;
   detection means for detecting light derived from the living object;
   converting means for converting the detected light into a first electric signal; and
   calculation means for performing a first calculation process on the first electric signal to output a second electric signal representing a change in concentration of hemoglobin at the predetermined position of the part of the living object wherein the change in concentration of hemoglobin is caused by injecting a blood diluting liquid as a tracer into the living object, performing a second calculation process on the second electric signal to calculate at least one of a blood flow, a degree of oxidation of hemoglobin, and an absolute concentration of hemoglobin.

2. A diagnostic device according to claim 1, wherein said calculation means calculates the blood flow in the predetermined position of the part of the living object based on the absolute concentration of hemoglobin calculated by said calculation means.

3. A diagnostic device according to claim 1, wherein said calculation means calculates a passage time required for the blood diluting liquid injected into the living object to pass the predetermined position of the part of the living object, and calculates the blood flow based on the calculated passage time.

4. A diagnostic device according to claim 1, wherein said calculating means outputs a third signal representing changes in concentration of oxyhemoglobin and a fourth signal representing changes in concentration of deoxyhemoglobin, and wherein said calculating means calculates at least one of the blood flow, the degree of oxidation of hemoglobin and the absolute concentration of hemoglobin based on at least one of the third signal and the fourth signal.

5. A diagnostic device according to claim 4, wherein said irradiation means alternately irradiates the predetermined position of the part of the living object with light having at least two types of wavelength to obtain the third signal and the fourth signal.

6. A diagnostic device according to claim 5, wherein the light irradiated by said irradiation means to obtain the third signal and the fourth signal has wavelengths of about 775 nm and about 825 nm, respectively.

7. A diagnostic device according to claim 6, wherein the blood diluting liquid has a light absorption coefficient which is negligibly smaller than light absorption coefficients of oxyhemoglobin and deoxyhemoglobin.

8. A diagnostic device according to claim 7, wherein the blood diluting liquid is physiological salt solution.

9. A diagnostic device comprising:
   blood volume measuring means for measuring a volume of blood existing in a part of a living object and providing a measured value of the volume of blood;
   injection means for injecting physiological salt solution as a tracer into the living object;
   time measuring means for measuring a time required for the physiological salt solution to pass through a predetermined position of the part of the living object and providing a passage time; and computing means for computing a blood flow based on the measured value of the blood of volume and the passage time, wherein said blood volume measuring means comprises a light source irradiating near-infrared light on the predetermined position of the part of the living object, a photomultiplier tube receiving the near-infrared light derived from the living object, and processing unit processing the near infrared light derived from the living object to calculate the volume of blood.

10. A diagnostic device according to claim 9, wherein said time measuring means comprises integrating means for integrating a change in concentration of hemoglobin and producing an integrated value and a detecting means for detecting a maximum change in concentration of hemoglobin and producing a maximum value, said time measuring means calculating the passage time based on the integrated value and the maximum value.

11. A diagnostic device according to claim 10, wherein said integrating means comprises first detection means for detecting a start time at which the physiological salt solution starts passing the predetermined position of the part of the living object, and second detection means for detecting an end time at which the physiological salt solution ends passing the predetermined position, and wherein said integrating means performs integration of the change in concentration of hemoglobin in a range between the start time and the end time.

12. A diagnostic device according to claim 11, wherein said computing means outputs a first signal representing changes in concentration of oxyhemoglobin and a second signal representing changes in concentration of deoxyhemoglobin, and wherein said calculating means calculates at least one of the blood flow, a degree of oxidation of hemoglobin and an absolute concentration of hemoglobin based on at least one of the first signal and the second signal.

13. A diagnostic device according to claim 9, wherein said light source alternately irradiates the predetermined position of the part of the living object with light having at least two types of wavelength to obtain the first signal and the second signal.

14. A diagnostic device according to claim 13, wherein the light irradiated by said light source to obtain the first signal and the second signal has wavelengths of about 775 nm and about 825 nm, respectively.

\* \* \* \* \*